(12) United States Patent
Neumann (10) Patent No.: US 11,625,673 B2
(45) Date of Patent: Apr. 11, 2023

(54) METHODS AND SYSTEMS FOR PATH SELECTION USING VEHICLE ROUTE GUIDANCE

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 16/890,839

(22) Filed: Jun. 2, 2020

(65) Prior Publication Data

US 2021/0374669 A1 Dec. 2, 2021

(51) Int. Cl.

| | | |
|---|---|---|
| *G06Q 10/08* | (2012.01) | |
| *G06Q 50/12* | (2012.01) | |
| *G06N 20/00* | (2019.01) | |
| *G06Q 30/02* | (2012.01) | |
| *G06Q 10/04* | (2012.01) | |
| *G01C 21/34* | (2006.01) | |
| *G16H 50/20* | (2018.01) | |
| *G16H 20/60* | (2018.01) | |

(Continued)

(52) U.S. Cl.
CPC ... *G06Q 10/08355* (2013.01); *G01C 21/3407* (2013.01); *G01C 21/3446* (2013.01); *G06N 20/00* (2019.01); *G06Q 10/047* (2013.01); *G06Q 30/0202* (2013.01); *G06Q 50/12* (2013.01); *G16H 20/60* (2018.01); *G16H 50/20* (2018.01)

(58) Field of Classification Search
None
See application file for complete search history.

(56) References Cited

U.S. PATENT DOCUMENTS 11,205,212 B1 * 12/2021 Lacono .............. G06Q 30/0641
11,244,752 B2 * 2/2022 Grimmer ............ G06F 16/9535
(Continued)

OTHER PUBLICATIONS

Rowland, M., Beyoncé Is Using Artificial Intelligence To Help You Eat Vegan, Apr. 24, 2018, Forbes (Year: 2018).*
https://doordash.engineering/2020/02/28/next-generation-optimization-for-dasher-dispatch-at-doordash/.

*Primary Examiner* — Brian M Epstein
*Assistant Examiner* — Sara Grace Brown
(74) *Attorney, Agent, or Firm* — Caldwell Intellectual Property Law (57) ABSTRACT

A system for path selection using vehicle route guidance includes computing device configured to receive a plurality of requests for a plurality of alimentary combinations and a plurality of destinations, wherein each request specifies an alimentary combination of the plurality of alimentary combinations to be assembled by at least an alimentary provider and a destination of the plurality of destinations, compute a projected nutritionally guided order volume using a first machine-learning process, determine a plurality of assembly times, the plurality of assembly times including an assembly time for each alimentary combination, as a function of the nutritionally guided order volume, generate a plurality of predicted routes as a function of the determined assembly times, and pair a predicted route of the plurality of predicted routes with a courier, wherein pairing further pairing, with the courier, the predicted route that optimizes an objective function.

16 Claims, 4 Drawing Sheets

(51) Int. Cl.
    *G06Q 10/0835*     (2023.01)
    *G06Q 30/0202*     (2023.01)
    *G06Q 10/047*      (2023.01)

(56) References Cited

U.S. PATENT DOCUMENTS

| | | | |
|---|---|---|---|
| 2009/0012923 A1* | 1/2009 | Moses | G06Q 10/10 |
| | | | 706/46 |
| 2013/0151357 A1* | 6/2013 | Havas | G06Q 50/12 |
| | | | 705/15 |
| 2018/0075404 A1* | 3/2018 | Hendrickson | G06Q 50/30 |
| 2018/0308143 A1* | 10/2018 | Chan | G06Q 30/0643 |
| 2018/0315148 A1* | 11/2018 | Luo | G06Q 10/06313 |
| 2019/0073601 A1* | 3/2019 | Alkan | G06Q 30/00 |
| 2019/0120640 A1* | 4/2019 | Ho | G06Q 10/04 |
| 2019/0164126 A1 | 5/2019 | Chopra et al. | |
| 2019/0168902 A1* | 6/2019 | Wise | A47J 36/32 |
| 2019/0188608 A1* | 6/2019 | Guru | G06Q 10/02 |
| 2019/0205999 A1* | 7/2019 | Gutnik | G06Q 50/12 |
| 2019/0290172 A1* | 9/2019 | Hadad | G06N 20/00 |
| 2019/0370915 A1* | 12/2019 | Garden | G06Q 10/1097 |
| 2020/0066181 A1* | 2/2020 | Hadjigeorgiou | G16H 20/60 |
| 2020/0074354 A1* | 3/2020 | Qin | G06N 3/08 |
| 2020/0074524 A1* | 3/2020 | Smith | G06Q 50/12 |
| 2020/0098466 A1* | 3/2020 | Murdoch | G16H 20/60 |
| 2020/0104962 A1* | 4/2020 | Aich | G06Q 50/30 |
| 2020/0114523 A1* | 4/2020 | Knuepfel | B25J 11/00 |
| 2020/0152080 A1* | 5/2020 | Wu | G06Q 30/0631 |
| 2020/0334628 A1* | 10/2020 | Goldberg | G06Q 10/087 |
| 2020/0342520 A1* | 10/2020 | Pandey | G06Q 50/12 |
| 2021/0256592 A1* | 8/2021 | Lee | G06Q 30/0635 |
| 2021/0306280 A1* | 9/2021 | Dorofiyenko | G06Q 50/30 |

* cited by examiner

METHODS AND SYSTEMS FOR PATH SELECTION USING VEHICLE ROUTE GUIDANCE

FIELD OF THE INVENTION

The present invention generally relates to the field of path selections. In particular, the present invention is directed to methods and systems for path selection.

BACKGROUND

Efficient path selection using vehicle route guidance is an increasingly vital process for provisioning of alimentary combinations. However, existing methods for path selection using vehicle route guidance suffer from inaccuracy in predictions used to support further computations.

SUMMARY OF THE DISCLOSURE

In an aspect, a method of path selection using vehicle route guidance includes receiving a plurality of requests for a plurality of alimentary combinations and a plurality of destinations, wherein each request specifies an alimentary combination of the plurality of alimentary combinations to be assembled by at least an alimentary provider, and a destination of the plurality of destinations. The method includes computing a projected nutritionally guided order volume using a first machine-learning process. The method includes determining a plurality of assembly times, the plurality of assembly times including an assembly time for each alimentary combination, as a function of the nutritionally guided order volume. The method includes generating a plurality of predicted routes as a function of the determined assembly times, wherein each predicted route of the plurality of predicted routes includes a retrieval from the at least an alimentary provider and at least a destination, of the plurality of destinations. The method includes pairing a predicted route of the plurality of predicted routes with a courier, wherein pairing includes generating an objective function based on a plurality of objectives and pairing, with the courier, the predicted route that optimizes the objective function.

In another aspect, a system for path selection using vehicle route guidance includes a computing device configured to receive a plurality of requests for a plurality of alimentary combinations and a plurality of destinations, wherein each request specifies an alimentary combination of the plurality of alimentary combinations to be assembled by at least an alimentary provider and a destination of the plurality of destinations, compute a projected nutritionally guided order volume using a first machine-learning process, determine a plurality of assembly times, the plurality of assembly times including an assembly time for each alimentary combination, as a function of the nutritionally guided order volume, generate a plurality of predicted routes as a function of the determined assembly times, wherein each predicted route of the plurality of predicted routes includes a retrieval from the at least an alimentary provider; and at least a destination, of the plurality of destinations, and pair a predicted route of the plurality of predicted routes with a courier, wherein pairing further includes generating an objective function based on a plurality of objectives, and pairing, with the courier, the predicted route that optimizes the objective function.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments described in this disclosure establish projected assembly times for alimentary combinations based on nutritionally guided order volumes, and determine routes associated with orders based on the projected assembly times; route assignments to couriers are guided by use of an objective function. Objective function may be expressed as a loss function or score calculation, which may be evaluated using greedy algorithms, linear programming, mixed-integer linear programming, or the like. Projected guidance-free order volumes may further be used to generate projected assembly times. Embodiments may be used to generate real-time, efficient pairing of couriers with routes.

Figure 1:
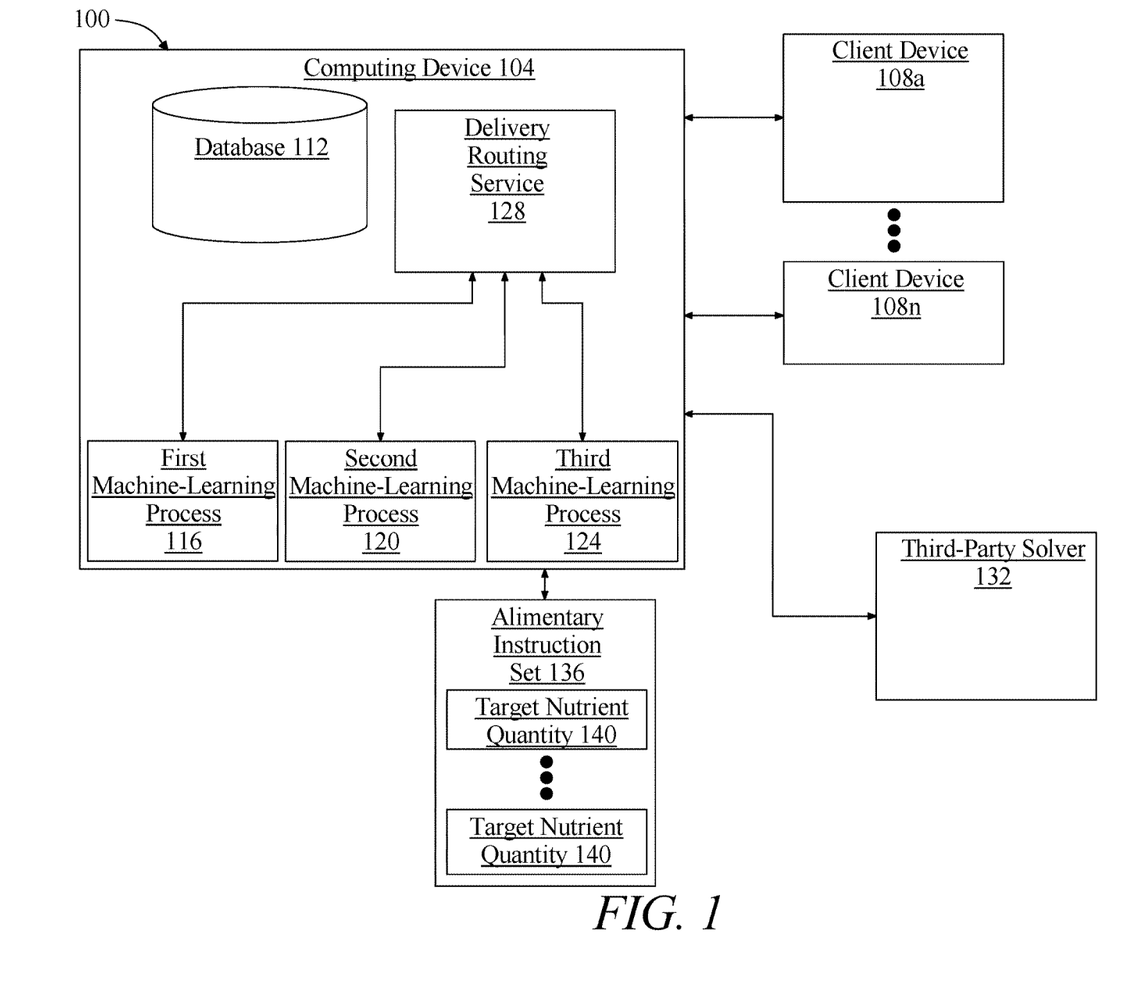
FIG. 1 is a block diagram illustrating an exemplary embodiment of a system for path selection.

Referring now to FIG. 1, an exemplary embodiment of a system for path selection using vehicle route guidance illustrated. System includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing device 104s in a first location and a second computing device 104 or cluster of computing device 104s in a second location. Computing device 104 may include one or more computing device 104s dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory between computing device 104s. Computing device 104 may be implemented using a "shared nothing" architecture in which data is cached at the worker, in an embodiment, this may enable scalability of system 100 and/or computing device 104.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 may communicate with a plurality of client devices 108 corresponding to users, alimentary providers, and/or couriers. Each client device of plurality of client devices 108 may be implemented in any manner suitable for implementation of computing device 104. As used in this disclosure, "alimentary providers" may include any entities that prepare alimentary combinations. As a non-limiting example, alimentary providers may prepare alimentary combinations at a restaurant. Other such alimentary providers may include any combination of one or more of the following: restaurants, bars, cafes, or other vendor of food or beverages, such as a hotel. System 100 may also communicate with one or more couriers. A "courier," as defined in this disclosure, is a person and/or device that transports alimentary combinations to one or more users requesting alimentary combinations. Such couriers may be on foot, or traveling by vehicle, such as a car, scooter, bicycle, etc. One or more couriers may be directed to one or more alimentary providers to receive an order placed by users and deliver the orders to the users located at corresponding destinations, which may include without limitation residential or commercial addresses. In some embodiments, the destinations may correspond to a particular geo-location determined by GPS or other coordinate system.

With continued reference to FIG. 1, computing device 104 may further connect to and/or include a database 112. Database 112 may be implemented, without limitation, as a relational database 112, a key-value retrieval database 112 such as a NOSQL database 112, or any other format or structure for use as a database 112 that a person skilled in the art would recognize as suitable upon review of the entirety of this disclosure. Database 112 may alternatively or additionally be implemented using a distributed data storage protocol and/or data structure, such as a distributed hash table or the like. Database 112 may include a plurality of data entries and/or records as described above. Data entries in a database 112 may be flagged with or linked to one or more additional elements of information, which may be reflected in data entry cells and/or in linked tables such as tables related by one or more indices in a relational database 112. Persons skilled in the art, upon reviewing the entirety of this disclosure, will be aware of various ways in which data entries in a database 112 may store, retrieve, organize, and/or reflect data and/or records as used herein, as well as categories and/or populations of data consistently with this disclosure. In some embodiments, network data, or other information such as user information, courier information, and alimentary provider information, may be stored in and/or retrieved from database 112.

Still referring to FIG. 1, users interacting with the client devices 108 may communicate with system 100 to request, search for, and/or browse for alimentary combinations. An "alimentary combination," is defined for the purposes of this disclosure as a combination of ingredients that an alimentary provider and/or alimentary provider device indicates may be provided, for instance and without limitation in the form of a meal. Various users, alimentary providers, and couriers may transmit information related to one or more orders to computing device 104 via corresponding client devices 108. As previously described, such information may include order information, payment information, activity updates, timestamps, location information, or other appropriate electronic information. System may utilize this transmitted information to batch orders and assign optimal routes to couriers for pickup and delivery of order for perishable goods. In another example, a software application executed on a mobile device, with proper permissions, may use a navigational facility global positioning system (GPS) capabilities to determine the user's location and automatically update the network with a user's location, whether in numerical terms such as latitude and longitude coordinates, and/or in relative or user-related terms such as "at home," "at work," in a particular municipality, or any other characterization of a geographical location and/or area.

With continued reference to FIG. 1, computing device may be configured to implement a first machine-learning process 116 for computation of nutritionally guided order volumes as described in further detail below. A second machine-learning process 120 may be used to determine a guidance-free order volume as described in further detail below. A third machine-learning process 124 may be implemented on computing device 104 to determine assembly times as set forth in further detail below. Computing device 104 may be configured to include a delivery routing system 128 to calculate projected routes and/or to perform pairing algorithm to offer couriers a plurality of received orders. In some embodiments, the delivery routing system 128 may optimize parings of routes with couriers; alternatively or additionally, a third-party solver 132 may perform some optimization calculations. Computing device 104 may receive and/or generate an alimentary instruction set 136 as described in further detail below; alimentary instruction set may include a plurality of target nutrient quantities 140.

Figure 2:
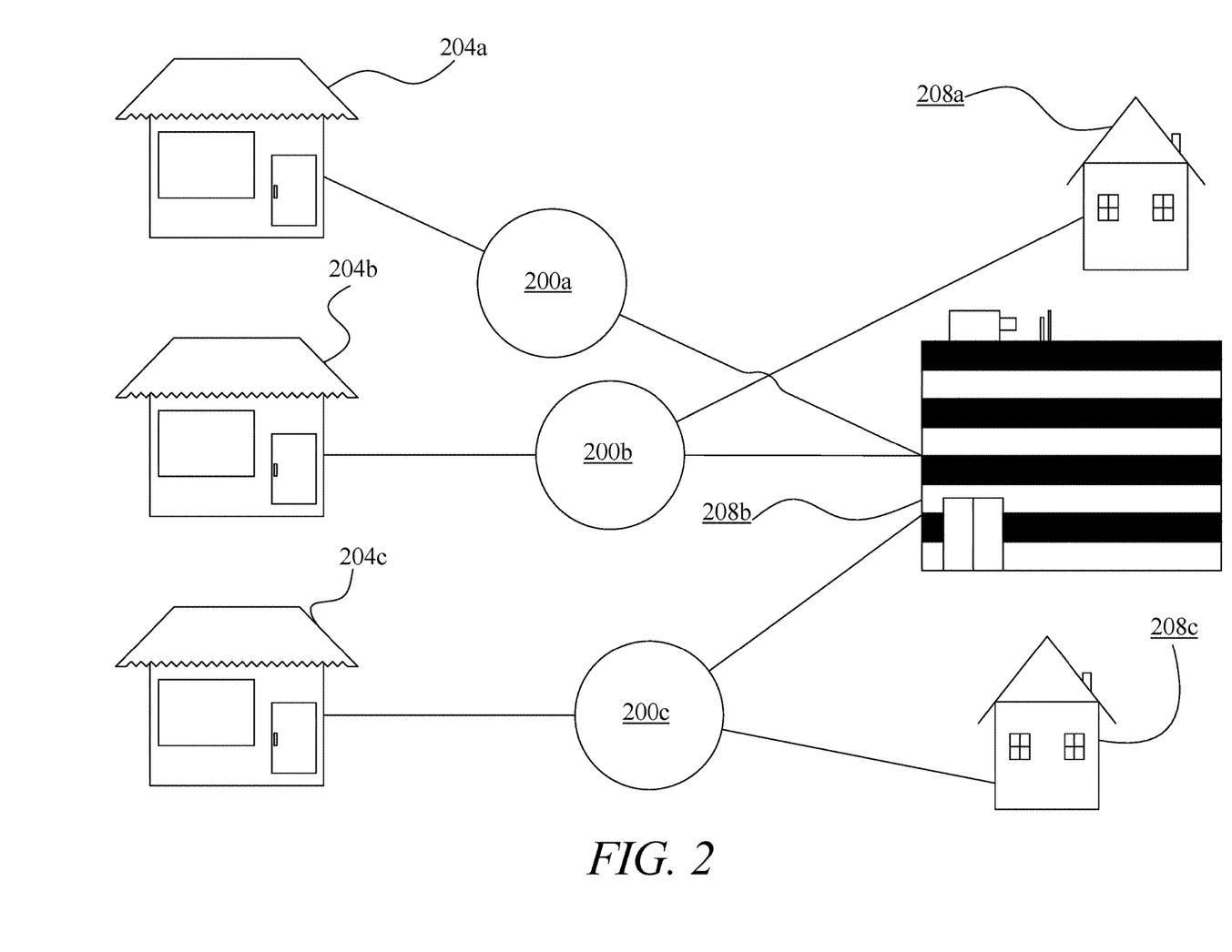
FIG. 2 is a schematic diagram illustrating an exemplary embodiment of a plurality of routes.

Referring now to FIG. 2, computing device 104 may implement methods as described in further detail below to compute, select, and/or pair a plurality of paths 200*a-c* from alimentary providers to users with couriers; a path assigned to a courier may include a single path from a single alimentary providers 204*a-c* to users 208*a-c*. For instance, a user 208*a-c* may order food from a restaurant 204*a-c* by using a mobile device application that places the order through system. In some instances, user may also access system through the Internet via a computer, laptop, tablet, or the like. When user orders alimentary combinations through system, a resulting order may prepared at an alimentary provider site, where a courier may then pick up the order and deliver the order from the alimentary provider site to the user; courier may alternatively or additionally deliver a plurality of orders from one or more alimentary providers to one or more users.

Still referring to FIG. 2, delivery events associated with delivery of alimentary combinations may fall on a timeline. A timeline may include various events that occur when an order is placed by a user, on an alimentary provider timeline and a courier timeline. An alimentary provider timeline or courier timeline may include additional or fewer events than described here. Events in a timeline may be tracked via transmission between a server system and a client device 108 associated with one or more couriers, alimentary providers, and/or users, for instance as described above. As used herein, client devices 108 associated with users may be referred to as "user devices," client devices 108 associated alimentary providers may be referred to as "alimentary provider devices," and client devices 108 associated with couriers may be referred to as "courier devices."

Still referring to FIG. 2, events that occur on an alimentary provider timeline may include order creation, order placement, order confirmation, order ready, and order pickup. An order creation may occur when the system receives an order created by a user. The order may be received at the server system. The order may then be routed to the designated alimentary provider. In some embodiments, the order is routed to the designated alimentary provider by transmitting information corresponding to the order from the server to an alimentary provider device. An order placement event may occur when the order is received at an alimentary provider device. In some embodiments, alimentary provider may acknowledge receipt of an order by transmitting a confirmation, which may trigger an order confirmation event. Order confirmation may signal that preparation of an order has begun by alimentary provider. In some embodiments, a period of time between order creation and order confirmation may be referred to as a kitchen latency. An order ready event may subsequently occur when preparation of alimentary combinations in the order is completed and the order is ready for pickup by a courier. Event may be triggered by an alimentary provider confirmation that order is ready. Such confirmation may be transmitted by alimentary provider device to computing device 104. Alimentary provider may then wait for a courier to arrive for retrieval of order. When a courier arrives and picks up order, an order pickup event may occur; this event may also be triggered by an alimentary provider confirmation that a courier has received order. In some embodiments, events that occur on a courier timeline may overlap or correspond with one or more events on an alimentary provider timeline. Events on courier timeline may include order creation, order assignment, parked at alimentary provider, arrival at alimentary provider, order pickup, return to vehicle, parked at user, and/or order delivered.

In some embodiments, order assignment may be triggered by confirmation of acceptance of the order by a courier, for instance after a predicted route has been paired with a courier as described in further detail below. System may transmit a notification to a courier device corresponding to courier. In some embodiments, a period of time between order creation and order assignment may be known as assignment latency. When order assignment occurs may depend on various factors, including a distance of courier from alimentary provider, a travel time of the courier to the alimentary provider, traffic, time of day, or the like. In some embodiments, order assignment may not occur until the order has been confirmed by alimentary provider or is being prepared by the alimentary provider. In some embodiments, order assignment may not occur until alimentary provider has confirmed that order is ready for retrieval.

Still referring to FIG. 2, once an order is assigned courier may travel to alimentary provider location to pick up the order. Courier may then pick up order upon arrival at alimentary provider location, and trigger order pickup. In some embodiments, the system may perform one or more processes and/or process steps as described in further detail below to assign orders and route couriers such that the arrival at alimentary provider coincides with order ready. This may optimize the actions of the courier and the alimentary provider to minimize down time, which may occur where courier arrives before the alimentary provider has completed the order, or where the alimentary provider has completed the order before the courier arrives.

In some embodiments, and with further reference to FIG. 2, additional events may be tracked between order assignment and arrival at alimentary provider. For example, a courier may travel to an alimentary provider location by vehicle and then park her vehicle in an appropriate location to reach the alimentary provider. In some embodiments, courier may confirm that vehicle is parked by transmitting a confirmation from the courier device to the server, thereby triggering parked at alimentary provider event. Courier may then have to walk or otherwise travel from parking location to alimentary provider. An arrival at alimentary provider event may also occur when courier has arrived at alimentary provider location. A confirmation of courier's arrival may be sent by courier device and/or alimentary provider device. In various embodiments, tracking these additional events may provide more accuracy of predictions and/or route assignments as described in further detail below. In some embodiments, courier may have to wait for order to be completed. After order retrieval, courier may then travel to user location to complete delivery of the order at order delivery. Order delivery may occur when the order has been given to the user. Order delivery may be triggered by confirmation of the delivery by the user or the courier via corresponding devices.

In some embodiments, and still referring to FIG. 2, a predicted estimated time of completion may be generated for each event on timelines. In some embodiments, predicted estimated times of completion for one or more events may be transmitted to various client devices 108, such as user devices, alimentary provider devices, and courier devices. The predicted estimated times of completion may further be used for delivery routing system 128 for assignment of orders to couriers and alimentary providers for delivery. In an embodiment, use of timelines as described above divides a delivery process into distinct delivery events that are more predictable because they depend on unique features of an alimentary provider and/or courier, such as order protocol, food preparation speed, driving speed, or the like.

Figure 3:
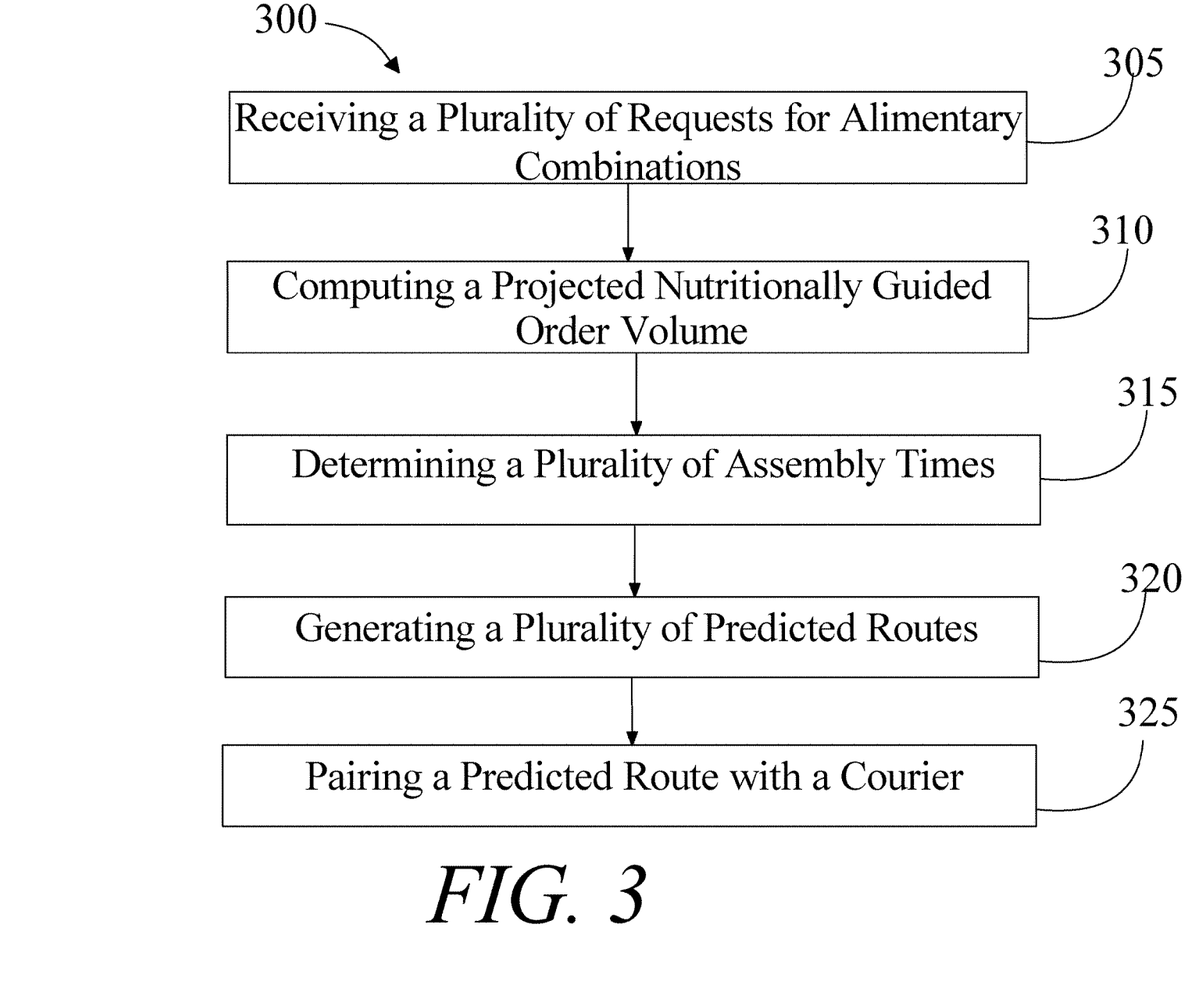
FIG. 3 is a flow diagram illustrating a methods of path selection.

Referring now to FIG. 3, an exemplary embodiment of a method 300 of path selection using vehicle route guidance is illustrated. At step 305, a computing device 104 receives a plurality of delivery requests for a plurality of alimentary combinations and a plurality of destinations. Each request of plurality of requests includes an alimentary combination of the plurality of alimentary combinations to be assembled by at least an alimentary provider, where including an alimentary combination signifies inclusion of an identifier of the alimentary combination. Each request of plurality of requests includes a destination of plurality of destinations. In an embodiment, an order may be placed by a user on a corresponding user device as described above. Order may be placed in a web browser or an application installed on user device. Order information may be transmitted via network. Destination may include location information corresponding to a location for delivery of order. For example, a location of the user device may be determined via GPS and/or other navigational facilities. As another example, location information may include an address corresponding to user. Order placement may further include additional information, such as ordered items, payment information, and other user information. In some embodiments, receipt of an order may correspond to an order creation event as described above.

In some embodiments, and still referring to FIG. 3, updates to order may be received by computing device 104. In some embodiments, order updates may include addition or removal of various items in an order, cancellation of the order, changes in delivery location, or the like. In some embodiments, updates to the order may be factored into a predicted time of order delivery. In some embodiments, a confirmation of delivery may be received from user device. For example, user may transmit a confirmation of delivery via user device once order is received from a courier. Alternatively or additionally, confirmation of delivery may be transmitted by a courier via a corresponding courier device.

At step 310, and still referring to FIG. [[1]], computing device 104 computes a projected nutritionally guided order volume. A "nutritionally guided order volume," as used in this disclosure, is a number of orders received in a given period of time in that are generated pursuant to an alimentary instruction set, which may include one or more recommended nutritional quantities. Generation and use of alimentary instruction sets may be performed by computing device 104 and/or another element of system 100, for instance and without limitation as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," published as US 2021/0005317 A1, the entirety of which is incorporated herein by reference. In an embodiment, an alimentary instruction set is a data structure containing a solution and/or suggestion to nourishment requirements or constitutional or chemical deficiencies. For example, a recommendation to increase iron intake based on at least a biological extraction from a user reflecting anemia may be utilized to generate an alimentary instruction set that includes a suggestion for a user to increase consumption of organ meats and green leafy vegetables. In yet another non-limiting example, an alimentary instruction set may contain a component seeking to remedy a B vitamin deficiency of a user based on a comprehensive instruction set showing blood levels of B vitamins below normal acceptable values. Alimentary instruction set may include suggested foods, meals, ingredients, medications, nutrients, supplements, vitamins, homeopathic remedies, and the like that a user may consider consuming. For example, a user with a diagnostic output such as hypothyroidism may be recommended to consume three brazil nuts each week and to consume a selenium supplement. In yet another non-limiting example, a user with ulcerative colitis may be recommended to consume a grain free paleo diet. In yet another non-limiting example, an alimentary instruction set may include a recommendation for a supplement such as ubiquinol for a user with high blood pressure or a methylated b-complex for a user with a 5,10-methylenetetrahydrofolate mutation (MTHFR).

Still referring to FIG. 3, computing device 104 may compute projected nutritionally guided order volume using one or more scheduled nutritionally guided orders generated through computing device 104 and/or system 100 as described above; for instance, some number of users in a geographic region may have received alimentary instruction sets, for instance as described above, and/or may have scheduled one or more alimentary combinations to be prepared and/or consumed based on alimentary combinations, on a given date and/or at a given time.

In an embodiment, and still referring to FIG. 3, computing projected nutritionally guided order volume may include training a first machine-learning process 116 using training data associating past nutritionally guided order volumes with a plurality of past extrinsic circumstances, receiving at least a current extrinsic circumstance, and computing the projected nutritionally guided order volume as a function of the at least a current extrinsic circumstance using the machine-learning process. An "extrinsic circumstance," as used herein, is any parameter that may be used to predict nutritionally guided order, including without limitation a calendar date, time of day, season, one or more scheduled and/or spontaneous events such as sporting events, concerts, protests, conventions, or the like, current and/or forecasted weather, current and/or forecasted traffic, a volume of nutritionally guided orders that have already been received, a volume of guidance-free orders, as defined below, that have already been received, and/or a projected guidance-free volume as described in further detail below.

With continued reference to FIG. 3, a "machine learning process," as used in this disclosure, is a process that automatedly uses a body of data known as "training data" and/or a "training set" to generate an algorithm that will be performed by a computing device 104/module to produce outputs given data provided as inputs; this is in contrast to a non-machine learning software program where the commands to be executed are determined in advance by a user and written in a programming language.

Still referring to FIG. 3, "training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure. As a non-limiting illustrative example, training data used for first machine-learning process 116 may include a plurality of entries correlating extrinsic data, as described above, to past volumes of nutritionally guided orders; each element of past data may be archived and/or tracked on computing device 104 and/or other elements of system 100, with correlations according to timestamps of such recorded data. Computing device 104 may train first machine-learning process 116 and/or use first machine-learning process 116 using training data.

With continued reference to FIG. 3, computing device 104 may be designed and configured to perform first machine-learning process 116 and/or create a machine-learning model therewith using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Alternatively or additionally, and further referring to FIG. 3, computing device 104 may be designed and configured to perform first machine-learning process 116 and/or create a machine-learning model therewith by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Continuing to refer to FIG. 3, computing projected nutritionally guided order volume may include computing a per-provider nutritionally guided order volume. As used herein, a "per-provider nutritionally guided order volume" is a prediction for a volume of nutritionally guided orders that will be received by a particular provider. For instance, and without limitation, a separate regression algorithm and/or neural net may be trained and/or utilized to compute a per-provider nutritionally guided order volume for each alimentary provider. Neural network may include a plurality of subnetworks, each of which function as a predictive event model to generate a nutritionally guided order volume for a particular alimentary provider. In an embodiment, per-provider nutritionally guided order volumes may be aggregated using averaging, addition, or the like, to produce an overall and/or aggregate nutritionally guided order volume over a geographical region, which may include any geographical region as described in further detail below.

At step 315, and still referring to FIG. 3, computing device 104 determines a plurality of assembly times. An "assembly time," as used in this disclosure, is an amount of time that it takes an alimentary provider to prepare an alimentary combination, such that the alimentary combination is ready for delivery. In an embodiment, a plurality of assembly times includes an assembly time for each alimentary combination of plurality of alimentary combinations. Computing device 104 determines each assembly time of plurality of assembly times as a function of the nutritionally guided order volume. Nutritionally guided order volume may affect assembly time in various ways; for instance, an alimentary provider may have particular persons ingredients, and/or pieces of equipment that can process only a limited number of orders at a time, such that a nutritionally guided order volume above a certain volume may cause increasing delays in assembly of alimentary combinations.

Still referring to FIG. 3, computing device 104 may determine each assembly time of plurality of assembly times by performing a third machine-learning process 124. Third machine-learning process may be implemented using any machine-learning algorithm as described above, including without limitation performance of a regression algorithm, training a neural net, or the like. Computing device 104 may train third machine-learning process 124 using training data correlating inputs including past nutritionally guided order volumes to outputs representing past assembly times, where past assembly times, training data, and/or one or more models produced may be specific to alimentary provider. For instance, and without limitation some alimentary providers may be more likely to have increased assembly times as a result of grater nutritionally guided order volumes than others owing to factors such as limited staffing, facility sizes, equipment, prepared ingredient supplies, and the like. Computing device 104 may input projected nutritionally guided order volume, which may be combined with one or more additional inputs, to third machine-learning process 124, and output an assembly time for each alimentary provider of plurality of alimentary providers.

With continued reference to FIG. 3, inputs to third machine-learning process 124 may further include types of alimentary combinations. For example, certain dishes may be correlated with particular assembly times. Inputs may include order sizes; in some embodiments, more items within an order may correlate to longer assembly times. Inputs may include order prices. For instance, a sub-total price of an order may also correspond to order size or order preparation time and may be used as a proxy to order size; a larger sub-total may correlate to a larger number of items within the order. Additionally, more expensive items may take longer to make, due to more ingredients, more difficulty, or more specialization in preparation. Inputs may include one or more particular nutritional recommendations followed in preparing alimentary combinations; for instance, some nutritional recommendations may be more labor intensive, be more complex, or require ingredients that take longer to prepare such as ingredients that must be soaked, marinated, fermented, cooked slowly, or the like. Some processes for generating recommended meals may be more demand-sensitive, as they might require more skilled preparation or preparation by a limited number of persons and/or specialized equipment. Similarly, in some embodiments, a neural network and/or regression model used in third machine-learning process 124 may determine an average rate for time durations between one or more events on an alimentary provider timeline for a particular alimentary provider, for instance as described above. However, historical performance may also be input as parameters. Historical performance of a particular alimentary provider may also be input. This may include an average time duration between events on alimentary provider timeline for that particular alimentary provider. Neural network and/or regression model may use this factor to assign a particular state variable to a given alimentary provider to adjust predictions accordingly. For example, an average time for a particular alimentary provider to prepare a particular item may be tracked and determined. As an example, some alimentary providers may not transmit a confirmation of receipt of order, but instead immediately begin preparation of the order. Once an order has been complete, alimentary provider may then transmit a confirmation of receipt of order and confirmation of completion of order simultaneously. A neural network and/or regression model may determine an estimated time of completion prediction accordingly such that a delivery routing system 128 may appropriately assign a courier at the optimal time.

In an embodiment, and further referring to FIG. 3, plurality of assembly times may be used to determine optimal retrieval times for couriers to being delivery routes; accurate predictions may prevent courier downtime while awaiting a meal that has not completed preparation, alimentary combination downtime that may occur when an alimentary combination is ready for delivery and no courier is present. Furthermore, accurate prediction of alimentary assembly times may enable greater accuracy in route prediction and/or assignment as described in further detail below.

Still referring to FIG. 3, inputs may include one or more projected guidance-free order volumes. A "guidance-free order volume," as used in this disclosure, is a volume and/or number of orders that are not prepared according to an alimentary instruction set used within system 100. As a non-limiting example, an order making up part of guidance-free order volume may be an order by a person or a party of persons that decide to order a meal or a plurality of meals for a party, conference, special occasion, or the like, without regard to any kind of meal plan or instruction set as described above. Such guidance-free orders may be generated and/or received through a variety of services and platforms, some of which may be inside of system 100 while others be outside of system 100; thus guidance-free order volume may be measured and/or recorded less directly than nutritionally guided order volume.

In an embodiment, and still referring to FIG. 3, determining a plurality of assembly times may include computing a projected guidance-free order volume and determining the plurality of assembly times as a function of the projected nutritionally guided order volume and the projected guidance-free order volume. Computing guidance-free order volume may include training a second machine-learning process 120 using training data associating past guidance-free order volumes with a plurality of past extrinsic circumstances, which may include any extrinsic circumstances as described above, receiving at least a current extrinsic circumstance, and computing projected guidance-free order volume as a function of the at least a current extrinsic circumstance using the machine-learning process. second machine-learning process 120 may include any machine-learning process as described above, including without limitation a regression-based machine-learning process, a process implementing and/or training a neural net, or the like.

Further referring to FIG. 3, training data may include a plurality of entries correlating past extrinsic data to guidance-free order volumes. As a non-limiting example, certain dates may fall on holidays that are historically known to be busy days. Thus, certain holidays may be correlated with increased number of orders placed in general. Additionally, certain times of the day may be associated with greater volumes of orders. In some embodiments, a size of markets may correspond to the number of individuals in a certain market who are potential users, couriers, and/or alimentary providers of a product or service. As used herein, the term market may be used to mean either a particular alimentary provider, or a group of alimentary providers associated with a particular product type. However, in some embodiments, the term market may refer to the total users, couriers, and/or alimentary providers in a given area that is part of the on-demand delivery service. second machine-learning process 120 may identify particular market sizes as correlated with certain differences in times for order preparation. A size of markets may also correspond to new and more mature markets. For example, a newer market may be correlated with longer order preparation times in third machine-learning process 124, while more mature markets may be correlated with faster order preparation times. Computing device 104 may calculate a projected guidance-free order volume as a per-provider guidance-free order volume, which may project guidance-free order for each alimentary provider. In an embodiment, projected guidance-free order volume may be used to determine a likely current or near-future order volume in which a significant portion of orders originate from entities and/or devices outside of system 100. In some embodiments, entities not affiliated with system 100 or an operator thereof may not provide up-to-date order information to system 100; using machine learning to compute a projected guidance-free order volume using historical data, for instance as reported by and/or collected from alimentary providers, may enable system 100 to track overall demand, as well as demand driven by nutritionally guided orders in system 100, and thus more accurately determine assembly times, capacity of alimentary providers to fulfill needed orders, and/or a number of couriers needed within a given region.

At step 320, computing device 104 generates a plurality of predicted routes as a function of estimated assembly times. A "predicted route," as described in this disclosure, is a route that a courier may follow from one or more alimentary providers to one or more users, to deliver alimentary combinations. Each predicted route of the plurality of predicted routes includes at least one retrieval from at least an alimentary provider and at least a destination, of plurality of destinations. Plurality of predicted routes may include at least one compound route. A "compound route," as used in this disclosure, is a route to more than one destination and/or from more than one alimentary provider. For instance, a party of users may order a plurality of meals from different providers, which may be delivered together using a compound route. As a further example, a plurality of orders to different destinations may be grouped together based on shared potential courier travel paths.

Still referring to FIG. 3, generating plurality of predicted routes may include receiving delivery parameters corresponding one or more orders. Delivery parameters may include various factors or measurements that may affect the length of time between one or more tracked events, such as courier timeline events as described above. In various embodiments, delivery parameters may include time, date, traffic, weather, historical courier performance, and size of markets. Delivery parameters may further include the number of orders received, the number of items in an order, the type of dishes in an order, the sub-total of an order, the historical restaurant data; various other parameters may be used. Traffic information may be tracked in real-time. In some embodiments, traffic information may be tracked by a third-party application. In some embodiments, traffic data is updated in real-time, or constantly updated in near real-time. Parameters corresponding to weather may also inform traffic or order impact. For example, inclement weather may correlate with heavier traffic due to hazardous conditions. Inclement weather may also correlate with more orders placed since users may be more likely to stay indoors. Weather parameters may also correspond to change in demands for particular food types. For example, more ice cream may be ordered during hot days. Another input parameter may include fleet load factor, which corresponds to the ratio of number of orders outstanding to the number of couriers outstanding. In some embodiments, the higher this ratio of fleet load factors may correspond to an insufficient number of couriers, and thus longer time durations for events after order ready. Historical performance of a courier may be a record of the previous time durations between one or more events on courier timeline for a particular courier. This record may be compared to the average time durations between one or more events on courier timeline for all couriers within a given area. The neural network may use this factor to assign a particular state variable to a given courier to adjust predictions accordingly. For example, a given courier may have shorter time durations between particular events, such as between parked at alimentary provider and arrival at alimentary provider, as compared to the average for a given area. In some embodiments, historical performance parameters may be organized into aggregate units for a predetermined amount of time. For example, the historical performance of a courier or alimentary provider for a previous thirty day increment may be given higher weighted values. In some embodiments, historical performance parameters for days occurring before a previous thirty days may also be input with lower weighted values. In some embodiments, historical performance parameters for days occurring before a previous thirty (30) days may be discarded. In some embodiments, a machine-learning model and/or neural network may determine an average rate for time durations between one or more events on a courier timeline for couriers in a given predetermined area.

With continued reference to FIG. 3, computing device 104 may generate a predictive event model to generate the plurality of predicted routes. Predictive event model may include, without limitation, a machine-learning model; machine-learning model may include any machine-learning model as described above, including without limitation a regression model and/or neural net. Training data used by computing device 104 and/or another device in system may include a plurality training entries, each training entry correlating extrinsic data and/or other data describing circumstances that may affect a courier's performance to overall delivery times and/or intervals between events on a delivery and/or courier timeline as described above. There may be a plurality of predictive event models, which may include neural net models and/or regression models, for different courier timeline events, different couriers, or the like. Neural network may include a plurality of subnetworks, each of which function as a predictive event model to generate an estimated length of time for a particular interval of time between subsequent delivery events. As used herein, terms "subnetwork" and "event model" may be used interchangeably, unless otherwise noted. In some embodiments, each interval between events, such as those described above corresponding to a courier timeline, may be associated with a subnetwork. In other words, a particular predictive event model may predict a duration between one event to a subsequent event.

Still referring to FIG. 3, delivery parameters may be input into the corresponding predictive event model as weighted factors. In various embodiments, predictive event model may be trained to correlate various parameters with particular effects on time durations between successive events. For instance, a neural-net predictive event model may assign weights to parameters creating weighted factors. Such weights may be adjusted based on actual time of arrivals.

At step 325, and still referring to FIG. 3, computing device 104 pairs a predicted route of the plurality of predicted routes with a courier. "Pairing," as used in this disclosure, signifies assigning a predicted route to a courier. In an embodiment, computing device 104 may identify a plurality of currently active couriers. Couriers may indicate current activity to system 100; for instance, courier may enter a user command on a courier device indicating that courier is currently working. Computing device 104 may track positions, current activities, and likely times of arrival at different locations and/or timeline points of plurality of couriers using navigation facilities, beacons, and the like; courier status according to a courier timeline as described above may be used to determine courier availability for a route. For instance, as a courier travels to an alimentary provider location, courier device may transmit to computing device 104 a status update indicating courier is traveling to alimentary provider. In various embodiments, travel status may include a status of a vehicle corresponding to courier. For example, courier device may transmit a notification to computing device 104 that courier has parked his vehicle near the alimentary provider location. Upon a courier's arrival at an alimentary provider location, a confirmation of arrival at alimentary provider location may be received. In some embodiments, the confirmation of arrival at alimentary provider location may include a check-in status update input by the courier on the courier device. Once an order is provided to courier, a confirmation of order pickup may be received. In some embodiments, the confirmation of order pickup may be confirmed by the courier via the courier device. As previously described, the confirmation of order pickup may additionally, and/or alternatively, be confirmed by the alimentary provider via the alimentary provider device.

As a further non-limiting example, and still referring to FIG. 3, a courier may travel to a user location after order pickup. As courier travels to user location, a travel status so indicating may be received by computing device 104. In various embodiments, travel status may include a status of a vehicle corresponding to courier. For example, courier device may transmit a notification to computing device 104 system that the courier has returned to the vehicle after the order pickup. As another example, a courier device may transmit a notification to computing device 104 that a courier has parked his or her vehicle near a user location. As another example, courier may then park his or her vehicle in an appropriate location to reach a user. In some embodiments, courier may confirm that vehicle is parked by transmitting a confirmation from courier device to computing device 104. Courier may then have to walk or otherwise travel from a parking location to user location. A confirmation of order delivery may be received from courier device. In some embodiments, a confirmation of order delivery may be confirmed by courier via courier device. Confirmation of order delivery may additionally or alternatively be confirmed by a user via a user device.

Still referring to FIG. 3, a current location and/or travel status of a courier may be used to predict a length and/or duration of a route courier may be able to travel to deliver a given alimentary combination. A travel status of a courier may also be tracked after order pickup and before order delivery. If it is detected that a distance between a courier and an alimentary provider location increases, then it may be determined that the courier is leaving the alimentary provider location and traveling toward a courier vehicle. As another example, once a courier moves within a predetermined radius of a vehicle, proximity sensors may determine that return to vehicle event has occurred, and an additional travel status to user location may be received. Subsequently, if it is detected that a distance between a courier and the courier's vehicle increases, then it may be determined that the courier has parked the vehicle and is moving toward a user location to deliver an order.

In some embodiments, and with further reference to FIG. 3, a travel status of a courier at various points in a timeline may be tracked via a proximity system, which includes one or more beacons. For example, beacon sensors may be placed in a courier's vehicle, which may be configured to detect a beacon device corresponding to a courier location. In some embodiments, beacon device may be a client device associated with courier. Additionally, beacon sensors may be located at one or more alimentary provider locations. As courier, and a corresponding courier device, travels toward and away from various beacons, a real-time location of the courier may be tracked.

In various embodiments, and still referring to FIG. 3, tracking of events or milestones may provide guidance to an assignment or routing algorithm to efficiently route couriers. For instance, a geographic location and/or current order status of a courier may be used by computing device 104 to determine times of availability of courier to perform one or more deliveries on routes to which computing device 104 may pair courier. As a non-limiting example, a first courier that is geographically close to an alimentary provider, but traveling away from the alimentary provider to drop off an alimentary combination at a user may not be available at that alimentary provider as soon as a second courier at a comparable geographical distance that provided a status indicating the second courier has completed a delivery and is ready for a subsequent assignment. As a further example, a courier on the way to a first alimentary provider to retrieve a first alimentary combination may be a good candidate to be assigned a route retrieving a second alimentary combination from a nearby second alimentary provider, for instance where users to receive first and second alimentary combinations are also proximate to one another.

Still referring to FIG. 3, orders and/or requests for alimentary combinations may be filtered for a set of orders to be delivered currently. Orders may, for instance, be filtered according to a time threshold; for instance and without limitation, time threshold may limit orders and/or requests to those for which a corresponding projected assembly time from a current time falls below a threshold. An order and/or request for alimentary combination which is projected to complete after the threshold may be addressed in a subsequent iteration of route pairing process. Orders may be further filtered, as a non-limiting example, to exclude orders that have not yet been confirmed and/or paid for by a user placing each order, orders that have not been confirmed as received by a corresponding alimentary provider, or the like.

In some embodiments, and further referring to FIG. 3, possible routes associated with each feasible pairing may generated. In some embodiments, routes may generate based on road distances on a map. Such routes may be generated using mapping information stored on a database 112 on system and/or on a third-party device. In some embodiments, a route may simply be a straight line distance from a courier location to an order location. In some embodiments, routes for all feasible pairings may be generated in parallel.

Still referring to FIG. 3, a set of active couriers within a geographical region may be selected. For example, GPS data received from courier devices may be used to locate each courier; couriers that are located outside of a predetermined geometric region may be filtered out of a set of all active couriers. In some embodiments, the geographic areas may be fixed with a given radius that defines the active region; radius may be centered about an urban center, a population cluster of alimentary providers and/or users, or the like; alternatively or additionally, multiple areas may be determined using a predetermined radius around each alimentary provider corresponding to aggregated order requests. A geographical region may subsequently be created from a union of such areas. In some embodiments, a geographical region may be disconnected or include multiple separated sub-regions. In some embodiments, geographic region may expand to include a greater area during times of high order volumes. For example, geographic region may double in area during high order volumes to include additional couriers to meet demand. Geographic region may alternatively or additionally be expanded when projected nutritionally guided order volume and/or projected guidance-free order volume exceeds a threshold amount. Geographic region may increase and/or decrease based on a number of available couriers within geographic region. For instance, geographic region may be expanded or contracted to include active couriers such that a desired ratio of available couriers within the active region to orders created, projected nutritionally guided order volume, projected guidance-free order volume, and/or any combination and/or aggregation thereof; a minimum threshold may, without limitation, be set for any such ratio, where ratio below threshold may trigger geographic region expansion, a ratio above threshold may trigger geographic region contraction, and the like.

Still referring to FIG. 3, computing device 104 may perform one or more steps to find an optimal or most efficient route to pair with a courier. A set of optimized and/or more efficient pairings of courier to route may be performed, without limitation, by using a machine-learning process as described above; for instance, computing device 104 may input couriers and routes into a trained neural network and/or machine-learning model to automatically predict projected time values and expected time values based on trained factors including vehicle type, vehicle size, order size, type of food, or the like. Neural network and/or machine-learning model may be trained, without limitation, using a plurality of training elements, each of which may correlate a past courier and route pairing and/or set of pairings with a value to be optimized, such as overall delivery time, average overall delivery time across all pairings, or the like.

Further referring to FIG. 3, optimization may include, without limitation, initially sorting couriers and routes and/or orders associated therewith into related groups and generating pairings within groups. Sorting may be based at least partially on geographic data of couriers and orders and/or routes, such as current locations and/or geographic regions, such as rectangular sections of given area, which may form a grid on a map. Proximity of current locations of couriers and alimentary provider locations may be used to divide orders and/or routes and active couriers into sorted groups. For example, alimentary provider locations corresponding to orders may be grouped by sub-region. In some embodiments, sub-regions may be arbitrarily selected. Alternatively or additionally, orders and/or routes and couriers may be grouped by other factors, such as regional boundaries like freeways, rivers, neighborhood boundaries, or the like. For example, alimentary providers corresponding to the created orders may be grouped into sub-regions defined by roads such that the sub-regions may correspond to recognized neighborhoods. Other factors for sorting couriers and orders and/or routes include historical courier data which may indicate familiarity with particular areas. For example, a courier that has picked up orders from a particular area or alimentary provider may be grouped with a set of orders from such region and/or alimentary provider, even if another courier is closer in geographic proximity to an order pickup location of alimentary provider.

Still referring to FIG. 3, in an embodiment, geographical regions used for initial sorting may vary in size according to other factors; for instance, in busier locations, where business may be determined using projected nutritionally guided order volume, guidance-free order volume, and/or a combination thereof, smaller rectangular cells may be used than in areas that have lower degrees of business. As a further non-limiting example, in locations with high density of restaurants and other alimentary providers, smaller rectangular cells may be employed.

With continued reference to FIG. 3, a plurality of pairings may be generated. Pairings may include pairings of all possible routes with all active couriers; alternatively or additionally, pairings may only be made between couriers and routes and/or orders that have been sorted together, as described above, for instance into a group. Couriers within the sorted group may then be paired with the created orders in that group. In some embodiments, the delivery routing system 128 may offer multiple orders to the same courier. For example, multiple orders being delivered to user locations that are within a predetermined distance may be offered to the same courier to optimize a travel route for delivery. In some embodiments, predicted estimated times of arrival for order ready events of such multiple orders may be input to determine whether a single courier should be offered the opportunity to pick up the multiple orders. Routes associated with multiple orders may be combined to form compound routes as described above.

In some embodiments, and continuing to refer to FIG. 3, possible data pairings are filtered to eliminate infeasible pairings from a set of feasible pairings. Infeasible pairings may be determined using various factors as constraints, such as transportation mode, vehicle type, vehicle size, order size, and type of food, ordered items, and other information associated with the data values. For example, an order that includes an extra-large pizza as an order item may not be a feasible pairing with a courier using a bicycle as transportation. As another example, orders for temperature sensitive goods may only be paired with couriers with refrigeration capabilities. In some embodiments, all possible feasible pairings are generated in parallel. Infeasible pairings may be determined based on additional constraints including one or more of the following: vehicle type, vehicle size, order size, and type of food.

Still referring to FIG. 3, computing device 104 may compute a score associated with each pairing and select pairings to minimize and/or maximize the score, depending on whether an optimal result is represented, respectively, by a minimal and/or maximal score; a mathematical function, described herein as an "objective function," may be used by computing device 104 to score each possible pairing. Objective function may based on one or more objectives as described below. Computing device 104 may pair a predicted route, with a given courier, that optimizes objective function. In various embodiments a score of a particular route and courier pairing may be based on a combination of one or more factors, including route efficiency, route priority, a projected lateness of a route, a reliability of the route, a fit of the route, and/or a state effect of the route. Each factor may be assigned a score based on predetermined variables. In some embodiments, the assigned scores may be weighted or unweighted.

Still referring to FIG. 3, route efficiency may correspond to how fast a courier may complete the delivery of an order along a generated route. This may be estimated based on historical courier performance data, as well as real-time traffic information and other geographic data items. In some embodiments, vehicle type may also be considered. For example, a motorcycle or scooter may be assigned a higher score than a car for particular routes because a motorcycle may be able to split lanes in heavy traffic. Route priority may correspond to how soon an order will be ready for pickup. In other words, the route priority may correspond to a time at which a given order is likely to be available for retrieval, based for instance on assembly time as described above, as well as on a time at which an order was initiated. In some embodiments, orders with earlier order ready events may be assigned higher scores. Projected lateness of a route may correspond to the difference in time between an estimated delivery time initially projected for a route and an estimated delivery time, such as delivery event, which may be predicted by a system based on updates received. In some embodiments, an estimated delivery time projected for a route may be determined based on real-time traffic information and other geographic data items; this may also be determined based on historical courier performance data. In some embodiments, if the projected route delivery time is later than a predicted and/or requested time for delivery, then the route may be assigned a lower score. By contrast, if a projected route delivery time is earlier than a requested and/or predicted time for delivery, then a route may be assigned a higher score. In some embodiments, an estimated delivery time projected by a route may be compared to a predetermined time threshold; if a projected delivery time is beyond the time threshold, the route may be given a zero score.

With continued reference to FIG. 3, a reliability of a route may correspond to a variance around an estimation for each point along the route. This may also correspond to a probability that a courier will complete an associated delivery by an estimated delivery time projected for a route. In some embodiments, historical route data may be used to determine the reliability of a route. For example, if a particular generated route includes one or more individual route segments, each route segment may include historical travel durations based on previously paired routes and tracked courier performances; previous travel durations for each segment may be compared and a standard deviation may be determined. A route with a more segments including larger standard deviations may correspond to a less reliable route and given a lower score. A fit of a route may correspond to how well the route fits a courier, which may be based on vehicle type, vehicle capacity, historical courier performance, or the like. A state effect of a route may correspond to an effect of the route on a balance of supply and demand with regard to available couriers and created orders in system 100. For example, a route that would bring a courier into an area where more couriers are needed may be scored higher.

Still referring to FIG. 3, generation of objective function may include generation of a function to score and weight factors to achieve a route score for each feasible pairing. In some embodiments, pairings may be scored in a matrix for optimization, where columns represent routes and rows represent couriers potentially paired therewith; each cell of such a matrix may represent a score of a pairing of the corresponding route to the corresponding courier.

With continued reference to FIG. 3, assigning predicted route that optimizes the objective function further comprises performing a greedy algorithm process. A "greedy algorithm" is defined as an algorithm that selects locally optimal choices, which may or may not generate a globally optimal solution. For instance, computing device 104 may select pairings so that scores associated therewith are the best score for each order and/or for each courier. In such an example, optimization may determine the combination of routes such that each delivery pairing includes the highest score possible.

Still referring to FIG. 3, objective function may be formulated as a linear objective function. Which computing device 104 may solve using a linear program such as without limitation a mixed-integer program. A "linear program," as used in this disclosure, is a program that optimizes a linear objective function, given at least a constraint. For instance, and without limitation, objective function may seek to maximize a total score $\Sigma_{r \in R} \Sigma_{s \in S} c_{rs} x_{rs}$, where R is the set of all routes r, S is a set of all couriers s, $c_{rs}$ is a score of a pairing of a given route with a given courier, and $x_{rs}$ is 1 if a route r is paired with courier s, and 0 otherwise. Continuing the example, constraints may specify that each route is assigned to only one courier, and each courier is assigned only one route; routes may include compound routes as described above. Sets of routes may be optimized for a maximum score combination of all generated routes. In various embodiments, system 100 may determine combination of routes that maximizes a total score subject to a constraint that all deliveries are paired to exactly one courier. Not all couriers may receive a route pairing since each delivery may only be delivered by one courier. A mathematical solver may be implemented to solve for the set of feasible pairings that maximizes the sum of scores across all pairings; mathematical solver may implemented on computing device 104 and/or another device in system 100, and/or may be implemented on third-party solver.

With continued reference to FIG. 3, optimizing objective function may include minimizing a loss function, where a "loss function" is an expression an output of which an optimization algorithm minimizes to generate an optimal result. As a non-limiting example, computing device 104 may assign variables relating to a set of parameters, which may correspond to score components as described above, calculate an output of mathematical expression using the variables, and select a pairing that produces an output having the lowest size, according to a given definition of "size," of the set of outputs representing each of plurality of candidate ingredient combinations; size may, for instance, included absolute value, numerical size, or the like. Selection of different loss functions may result in identification of different potential pairings as generating minimal outputs. Objectives represented in an objective function and/or loss function may include minimization of delivery times. Objectives may include minimization of wait times by couriers at alimentary providers; wait times may depend, for instance and without limitation, on assembly times as described above. Objectives may include minimization of times delivery times in excess of estimated or requested arrival times.

Still referring to FIG. 3, a selected pairing may be transmitted to a user device to notify a user of information corresponding to an assigned courier, such as identification, contact information, or the like. In some embodiments, an order pairing may be transmitted to a courier device to notify assigned courier of information corresponding to an alimentary provider and/or user associated with the order, such as location, contact information, order information, or the like. In some embodiments, an order pairing may be transmitted to an alimentary provider device corresponding to the order pairing to notify an alimentary provider using alimentary provider device of information corresponding to user and/or courier, including contact information. Routes may be offered to carriers based on an optimized set of routes as determined above.

With continued reference to FIG. 3, a confirmation of order assignment may be received. In some embodiments, confirmation of order assignment may be an acceptance of the order assignment input by a courier on an associated courier device. Computing device 104 may receive a location of courier. In some embodiments, location of courier may be tracked and updated in real time. In some embodiments, location of courier may be tracked via an associated courier device, such as by using real-time GPS coordinates and/or beacons as described above. In some embodiments, additional events may be tracked between order pickup and order delivery. For example, courier may confirm return to a vehicle after order pickup at alimentary provider location.

It is to be noted that any one or more of the aspects and embodiments described herein may be conveniently implemented using one or more machines (e.g., one or more computing device 104s that are utilized as a user computing device 104 for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device 104) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device 104) and any related information (e.g., data structures and data) that causes the machine to perform any one of the methodologies and/or embodiments described herein.

Examples of a computing device 104 include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device 104 may include and/or be included in a kiosk.

Figure 4:
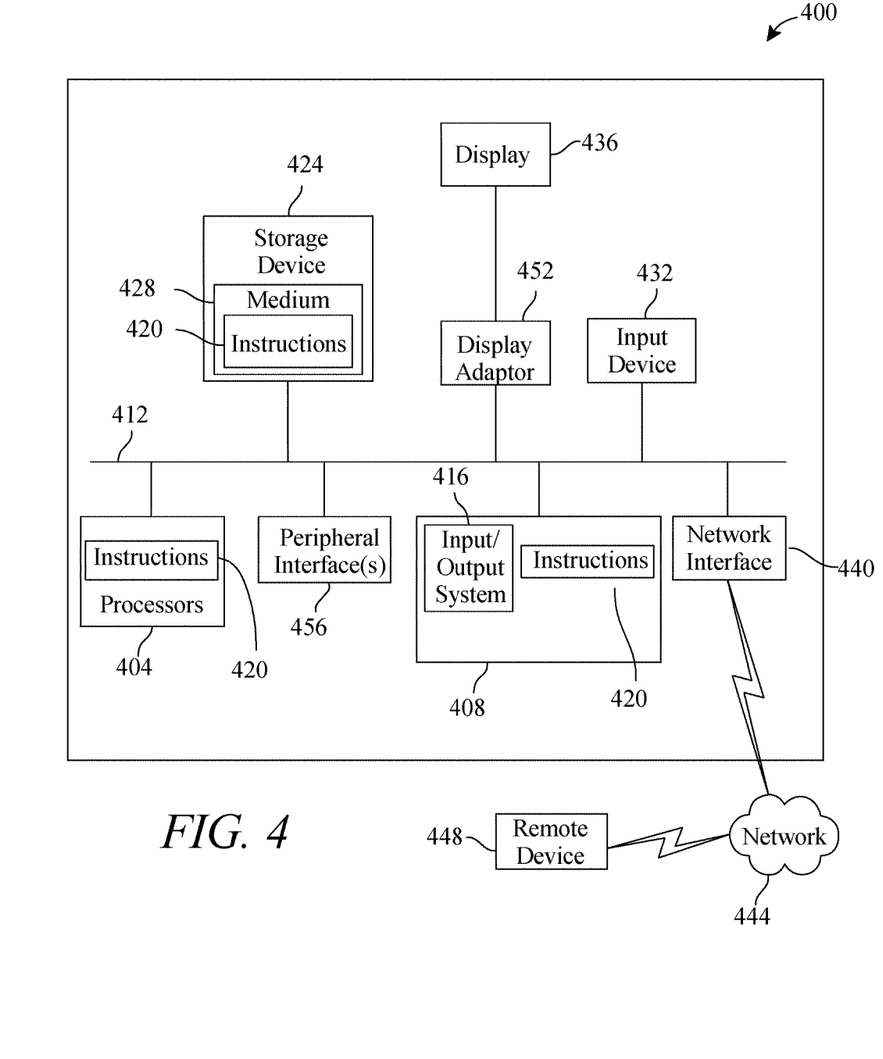
FIG. 4 is a block diagram of a computing system that can be used to implement any one or more of the methodologies disclosed herein and any one or more portions thereof.

FIG. 4 shows a diagrammatic representation of one embodiment of a computing device 104 in the exemplary form of a computer system 400 within which a set of instructions for causing a control system to perform any one or more of the aspects and/or methodologies of the present disclosure may be executed. It is also contemplated that multiple computing device 104s may be utilized to implement a specially configured set of instructions for causing one or more of the devices to perform any one or more of the aspects and/or methodologies of the present disclosure. Computer system 400 includes a processor 404 and a memory 408 that communicate with each other, and with other components, via a bus 412. Bus 412 may include any of several types of bus structures including, but not limited to, a memory bus, a memory controller, a peripheral bus, a local bus, and any combinations thereof, using any of a variety of bus architectures.

Processor 404 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 404 may be organized according to Von Neumann and/or Harvard architecture as a non-limiting example. Processor 404 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 408 may include various components (e.g., machine-readable media) including, but not limited to, a random-access memory component, a read only component, and any combinations thereof. In one example, a basic input/output system 416 (BIOS), including basic routines that help to transfer information between elements within computer system 400, such as during start-up, may be stored in memory 408. Memory 408 may also include (e.g., stored on one or more machine-readable media) instructions (e.g., software) 420 embodying any one or more of the aspects and/or methodologies of the present disclosure. In another example, memory 408 may further include any number of program modules including, but not limited to, an operating system, one or more application programs, other program modules, program data, and any combinations thereof.

Computer system 400 may also include a storage device 424. Examples of a storage device (e.g., storage device 424) include, but are not limited to, a hard disk drive, a magnetic disk drive, an optical disc drive in combination with an optical medium, a solid-state memory device, and any combinations thereof. Storage device 424 may be connected to bus 412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 424 (or one or more components thereof) may be removably interfaced with computer system 400 (e.g., via an external port connector (not shown)). Particularly, storage device 424 and an associated machine-readable medium 428 may provide nonvolatile and/or volatile storage of machine-readable instructions, data structures, program modules, and/or other data for computer system 400. In one example, software 420 may reside, completely or partially, within machine-readable medium 428. In another example, software 420 may reside, completely or partially, within processor 404.

Computer system 400 may also include an input device 432. In one example, a user of computer system 400 may enter commands and/or other information into computer system 400 via input device 432. Examples of an input device 432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 432 may be interfaced to bus 412 via any of a variety of interfaces (not shown) including, but not limited to, a serial interface, a parallel interface, a game port, a USB interface, a FIRE-WIRE interface, a direct interface to bus 412, and any combinations thereof. Input device 432 may include a touch screen interface that may be a part of or separate from display 436, discussed further below. Input device 432 may be utilized as a user selection device for selecting one or more graphical representations in a graphical interface as described above.

A user may also input commands and/or other information to computer system 400 via storage device 424 (e.g., a removable disk drive, a flash drive, etc.) and/or network interface device 440. A network interface device, such as network interface device 440, may be utilized for connecting computer system 400 to one or more of a variety of networks, such as network 444, and one or more remote devices 448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 104s, and any combinations thereof. A network, such as network 444, may employ a wired and/or a wireless mode of communication. In general, any network topology may be used. Information (e.g., data, software 420, etc.) may be communicated to and/or from computer system 400 via network interface device 440.

Computer system 400 may further include a video display adapter 452 for communicating a displayable image to a display device, such as display device 436. Examples of a display device include, but are not limited to, a liquid crystal display (LCD), a cathode ray tube (CRT), a plasma display, a light emitting diode (LED) display, and any combinations thereof. Display adapter 452 and display device 436 may be utilized in combination with processor 404 to provide graphical representations of aspects of the present disclosure. In addition to a display device, computer system 400 may include one or more other peripheral output devices including, but not limited to, an audio speaker, a printer, and any combinations thereof. Such peripheral output devices may be connected to bus 412 via a peripheral interface 456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of path selection using vehicle route guidance the method comprising:
   receiving, by a computing device, a plurality of requests, wherein each request comprises a respective alimentary combination to be assembled by alimentary providers and a respective destination;
   generating, by the computing device, a nutritionally guided order volume based on recommend nutritional quantities, using a first machine-learning process, wherein generating the nutritionally guided order volume comprises training the first machine-learning process using training data comprising associations between a plurality of past nutritionally guided order volumes and a plurality of past extrinsic circumstances and wherein the trained first machine-learning process is configured to receive the plurality of requests as an input and output the nutritionally guided order volume as a function of the plurality of requests;

computing, by the computing device, a guidance-free order volume as a function of at least a current extrinsic circumstance using a second machine-learning process;

determining, by the computing device, a plurality of assembly times as a function of the nutritionally guided order volume and the guidance-free order volume using a third machine-learning process, wherein each assembly time includes a respective assembly time for each alimentary combination of the plurality of requests;

determining, by the computing device, an average rate for time durations between events on an alimentary provider timeline for each of the alimentary providers using a neural network in the third machine-learning process and historical performance of each of the alimentary providers as inputs;

generating, by the computing device, a plurality of predicted routes, including at least a compound route as a function of shared potential courier travel paths, as a function of the determined assembly times, wherein each predicted route of the plurality of predicted routes comprises:
  a retrieval from at least a respective alimentary provider; and
  a respective destination of the plurality of requests; and pairing, by the computing device, a predicted route of the plurality of predicted routes with a courier using a greedy algorithm process, wherein pairing further comprises:
  generating an objective function based on a plurality of objectives, wherein the
    plurality of objectives includes at least historical courier data indicating a courier's familiarity with a particular area and;
    a numerical score representing a pairing between the courier and a respective predicted route of the plurality of predicted routes;
  pairing, with the courier, the predicted route according to the objective function and the numerical score representing a pairing between the courier and a respective predicted route of the plurality of predicted routes.

2. The method of claim 1, wherein computing the nutritionally guided order volume further comprises:
  training the first machine-learning process using training data correlating the past nutritionally guided order volumes with the plurality of past extrinsic circumstances;
  receiving at least a current extrinsic circumstance; and
  computing the nutritionally guided order volume as a function of the at least a current extrinsic circumstance using the machine-learning process.

3. The method of claim 1, wherein computing the nutritionally guided order volume further comprises computing a per-provider nutritionally guided order volume.

4. The method of claim 1, wherein computing a guidance-free order volume further comprises:
  training the second machine-learning process using training data correlating past guidance-free order volumes with a plurality of past extrinsic circumstances;
  receiving the at least a current extrinsic circumstance; and
  computing the guidance-free order volume as a function of the at least a current extrinsic circumstance using the second machine-learning process.

5. The method of claim 1, wherein computing the guidance-free order volume further comprises computing a per-provider guidance-free order volume.

6. The method of claim 1, wherein generating a plurality of predicted routes further comprises generating at least a compound route.

7. The method of claim 1, wherein pairing the predicted route of the plurality of predicted routes with the courier further comprises:
  identifying a plurality of currently active couriers; and
  assigning the predicted route to a courier of the plurality of active couriers.

8. The method of claim 1, wherein the objective function further comprises a mixed-integer program.

9. A system for path selection using vehicle route guidance the system comprising a computing device configured to:
  receive a plurality of requests, wherein each request comprises a respective alimentary combination to be assembled by alimentary providers and a respective destination;
  generate a nutritionally guided order volume based on recommend nutritional quantities, using a first machine-learning process, wherein generating the nutritionally guided order volume comprises training the first machine-learning process by a training data comprising associations between a plurality of past nutritionally guided order volumes with a plurality of past extrinsic circumstances and wherein the trained first machine-learning process is configured to receive the plurality of requests as an input and output the nutritionally guided order volume as a function of the plurality of requests and the training data;
  compute a guidance-free order volume as a function of at least a current extrinsic circumstance using a second machine-learning process;
  determine a plurality of assembly times as a function of the nutritionally guided order volume and the guidance-free order volume using a third machine-learning process, wherein each assembly time includes a respective assembly time for each alimentary combination of the plurality of requests;
  determine an average rate for time durations between events on an alimentary provider timeline for each of the alimentary providers using a neural network in the third machine-learning process and historical performance of each of the alimentary providers as inputs;
  generate a plurality of predicted routes, including at least a compound route as a function of shared potential courier travel paths, as a function of the determined assembly times, wherein each predicted route of the plurality of predicted routes comprises:
    a retrieval from at least a respective alimentary provider; and
    a respective destination of the plurality of requests; and
  pair a predicted route of the plurality of predicted routes with a courier using a greedy algorithm process, wherein pairing further comprises:
    generating an objective function based on a plurality of objectives, wherein the plurality of objectives includes:
      at least historical courier data indicating a courier's familiarity with a particular area and;

a numerical score representing a pairing between the courier and a respective predicted route of the plurality of predicted routes;

pairing, with the courier, the predicted route according to the objective function and the numerical score representing a pairing between the courier and a respective predicted route of the plurality of predicted routes.

10. The system of claim 9, wherein the computing device is further configured to compute the nutritionally guided order volume by:

training the first machine-learning process using training data correlating the past nutritionally guided order volumes with the plurality of past extrinsic circumstances;

receiving at least a current extrinsic circumstance; and computing the nutritionally guided order volume as a function of the at least a current extrinsic circumstance using the machine-learning process.

11. The system of claim 9, wherein the computing device is further configured to compute the nutritionally guided order volume by computing a per-provider nutritionally guided order volume.

12. The system of claim 9, wherein computing a guidance-free order volume further comprises:

training a second machine-learning process using training data correlating past guidance-free order volumes with a plurality of past extrinsic circumstances;

receiving at least a current extrinsic circumstance; and computing the nutritionally guided order volume as a function of the at least a current extrinsic circumstance using the second machine-learning process.

13. The system of claim 9, wherein computing the guidance-free order volume further comprises computing a per-provider guidance-free order volume.

14. The system of claim 9, wherein the computing device is further configured to generate a plurality of predicted routes by generating at least a compound route.

15. The system of claim 9, wherein the computing device is further configured to pair the predicted route with the courier:

identifying a plurality of currently active couriers; and assigning the predicted route to a courier of the plurality of active couriers.

16. The system of claim 9, wherein the objective function further comprises a mixed-integer program.

* * * * *